US006823714B2

(12) United States Patent
Megerle

(10) Patent No.: US 6,823,714 B2
(45) Date of Patent: Nov. 30, 2004

(54) SYSTEM AND METHOD FOR DETECTING HAZARDOUS MATERIALS INSIDE CONTAINERS

(75) Inventor: Clifford A. Megerle, Thousand Oaks, CA (US)

(73) Assignee: Lockheed Martin Corporation, Bethesda, MD (US)

(*) Notice: Subject to any disclaimer, the term of this patent is extended or adjusted under 35 U.S.C. 154(b) by 9 days.

(21) Appl. No.: 10/277,069

(22) Filed: Oct. 21, 2002

(65) Prior Publication Data

US 2004/0020267 A1 Feb. 5, 2004

Related U.S. Application Data

(60) Provisional application No. 60/330,673, filed on Oct. 26, 2001.

(51) Int. Cl.[7] .................................................. G01N 7/00
(52) U.S. Cl. ............................. 73/23.2; 73/23; 422/29
(58) Field of Search ......................... 73/23.2, 23, 23.36; 422/29

(56) References Cited

U.S. PATENT DOCUMENTS

| 3,915,339 A | 10/1975 | Matson |
| 3,998,101 A | 12/1976 | Bradshaw et al. |
| 4,580,440 A | * 4/1986 | Reid et al. .................. 73/31.07 |

(List continued on next page.)

FOREIGN PATENT DOCUMENTS

| EP | 0169057 | 1/1986 | ............ G01V/9/00 |
| JP | 02159554 | 12/1988 | |
| WO | WO 91/09307 | 6/1991 | |

OTHER PUBLICATIONS

Provisional Application Ser. No. 60/330,673 filed Oct. 26, 2001, Inventor: Clifford A. Megerle.
Copending Application, Ser. No. 10/282,868 filed Oct. 29, 2002, Inventors: John T. Bekert et al.
Copending Application, Ser. No. 10/314,631 filed Dec. 9, 2002, Inventors: Robert J. Felice et al.
Copending Application, Ser. No. 10/341,033, filed Jan. 13, 2003, Inventor: William Harris.
Copending Application, Ser. No. 10/201,169 filed Jul. 22, 2002, Inventor: John T. Swider.
Copending Application, Ser. No. 10/328,230 filed Dec. 23, 2002, Inventor: John T. Swider.
Copending Application, Ser. No. 10/328,264 filed Dec. 23, 2002, Inventors: James M Abulencia et al.
Copending Application, Ser. No. 10/289,810 filed Nov. 7, 2002, Inventor: Clifford A. Megerle.
WO 03/081214, Published PCT International Application, Publication Date Oct. 2, 2003, PCT/US02/34375 (12078–197PCT).

*Primary Examiner*—Hezron Williams
*Assistant Examiner*—Rodney Frank
(74) *Attorney, Agent, or Firm*—Perkins Smith & Cohen LLP; Jacob N. Erlich; Harvey Kaye

(57) ABSTRACT

A system and method for detecting hazardous materials inside containers includes an air distribution plate 20 that defines an air plenum AP with a series of openings 22 that function to distribute a flow of air. An air input port 26 and an air output port 28 are provided to allow connection to an air recirculation and sensor system 30 including an air mover 32 having an inlet duct 34 that is selectively connectable to the air outlet port 28 and an outlet duct 36 that is selectively connectable to the air inlet port 26 of the semi-trailer 10. Upon the creation of a recirculation air flow, the air recirculation and sensor system 30 functions to detect the presence of hazardous materials with in the containment.

17 Claims, 4 Drawing Sheets

U.S. PATENT DOCUMENTS

| | | | |
|---|---|---|---|
| 4,718,268 A | * | 1/1988 | Reid et al. .................. 73/19.01 |
| 4,764,351 A | | 8/1988 | Hennebert et al. |
| 4,987,767 A | * | 1/1991 | Corrigan et al. ............ 73/23.36 |
| 5,109,691 A | * | 5/1992 | Corrigan et al. ............ 73/23.36 |
| 5,322,603 A | | 6/1994 | Kameda |
| 5,345,809 A | * | 9/1994 | Corrigan et al. .............. 73/23.2 |
| 5,465,607 A | * | 11/1995 | Corrigan et al. ............ 73/23.36 |
| 5,470,546 A | | 11/1995 | Hall |
| 5,585,575 A | * | 12/1996 | Corrigan et al. .......... 73/863.71 |
| 5,591,117 A | | 1/1997 | Zelno |
| 5,700,426 A | | 12/1997 | Schmitthaeusler et al. |
| 5,841,038 A | | 11/1998 | Volz |
| 5,859,362 A | | 1/1999 | Neudorfl et al. |
| 5,942,699 A | | 8/1999 | Ornath et al. |
| 6,074,608 A | | 6/2000 | Matz ........................... 422/83 |
| 6,159,422 A | | 12/2000 | Graves et al. |
| 6,183,950 B1 | | 2/2001 | Madonna et al. |
| 6,295,860 B1 | | 10/2001 | Sakairi et al. |
| 6,324,927 B1 | | 12/2001 | Ornath et al. |
| 2001/0029793 A1 | | 10/2001 | Moler et al. ............. 73/863.22 |
| 2002/0124664 A1 | | 9/2002 | Call et al. |
| 2002/0126008 A1 | | 9/2002 | Lopez et al. |
| 2003/0071543 A1 | * | 4/2003 | Daghighian .................... 312/1 |
| 2003/0086821 A1 | | 5/2003 | Matthews .................... 422/29 |

* cited by examiner

SYSTEM AND METHOD FOR DETECTING HAZARDOUS MATERIALS INSIDE CONTAINERS

CROSS-REFERENCE TO RELATED APPLICATIONS

The present application claims the priority of previously filed provisional application Ser. No. 60/330,673 filed Oct. 26, 2001 for System and Method For Detecting Hazardous Material Inside Containers, and the entire content thereof is incorporated herein by reference.

BACKGROUND OF THE INVENTION

The present invention relates to a system and method for detecting hazardous materials inside containers and, more particularly, to a system and method for detecting hazardous materials inside shipping containers, such as semi-trailers cargo boxes, shipping containers, rail cars and the like, in which mail, merchandise, and goods are shipped.

All economies depend upon the physical shipment of materials for their functioning including the shipment of mail, merchandise, raw materials, and other goods. Typically, the materials are shipped in some type of shipping containment or cargo box. Such containments or boxes include semi-trailers, large trucks, and rail cars as well as inter-modal containers that are carried on container ships, off-loaded and carried by specially designed rail cars, and thereafter transferred to tractor-trailers for delivery to their final destination.

In some circumstances, it is desirable to subject the cargo to some type of inspection to determine the presence of hazardous or impermissible materials, including biological and chemical materials. In general, sophisticated sensing systems are known for the detection of hazardous biological and chemical materials. For example, such systems can include conventional laboratory facilities as well as mobile or semi-mobile units that can automatically or semi-automatically detect the presence of the undesired substance or substances. One such vehicle-mobile system is the Joint Biological Point Detection System (JBPDS) developed for the United States military and designed to detect the presence of a number of biological pathogens. Others include sensor or detectors for hazardous chemicals, explosives, illicit drugs, radioactive particles, and other hazardous materials. These sensors can be used single, or in combinations, to detect as many types of hazardous particles or vapors as required.

Currently when there is suspicious mail, it is all bulk irradiated as was done during the recent anthrax problem thereby delaying some mail for months and damaging or destroying some of the mail due to problems caused by the irradiation. For example some of this irradiated mail became brittle and pieces broke off.

U.S. Published Application No. US 2002/0126008 published Sep. 12, 2002 and filed Oct. 31, 2001 discloses use of sensors at various locations within a typical mail processing system to sense the presence of a harmful agent. This system is completely open to the ambient atmosphere. (The present application is based upon a provisional patent application filed Oct. 26, 2001.)

U.S. Published Application No. US 2002/0124664 published Sep. 12, 2002 and filed Feb. 1, 2002 discloses use of a mail sampling system used in a room separate from the remainder of a post office facility and in which there is an air intake fan and all outgoing air is filtered before release. Most often openings are formed in the parcels and mail for the sampling. The sampling system is said to determine whether mail is contaminated with a chemical or biological agent. (The present application is based upon a provisional patent application filed Oct. 26, 2001.)

U.S. Pat. Nos. 5,942,699 and 6,324,927 disclose a manner of collective sampling of cargo items for contaminants such as chemical residues. The cargo items are placed into a special airtight chamber and physically agitated, such as by vibration, to release particulates and vapors from the items, and bursts of high pressure air is sent into the chamber. Heated air may also be used.

U.S. Pat. No. 3,915,339 discloses use of pressurized air into a container to loosen and cause free flow of material therein move.

U.S. Pat. No. 3,998,101 discloses a method and apparatus for sampling the atmosphere in non-hermetically-sealed containers by enclosing baggage in a chamber and varying the air pressure cyclically to mix a portion of the air in the baggage with the air in the chamber and a vapor detector is used to detect the presence of explosives or drugs in the baggage.

U.S. Pat. No. 4,580,440 discloses a method of detecting a contraband substance in freight cargo in which the container is agitated to disturb particulates therein and samples are taken of the air containing such particulates. The collected particulates are heated to drive off vapors indicative of the contraband substance and the vapors are analyzed in a mass analyzer.

U.S. Pat. No. 4,718,268 discloses a method and apparatus for detecting a contraband substance in freight cargo similar to that of U.S. Pat. No. 4,580,440 mentioned above.

U.S. Pat. No. 4,764,351 discloses a sterilization method and apparatus using a gaseous agent for sterilizing a gas for use in treating materials.

U.S. Pat. No. 5,322,603 discloses a method of an apparatus for treating infections medical wastes is which large sizes of medical waste in a sealed body are exposed to microwaves and heat.

U.S. Pat. No. 5,470,546 discloses apparatus for storing and sterilizing bio-hazardous waste in which air is evacuated and pressurized steam is injected.

U.S. Pat. No. 5,591,117 discloses a method and an apparatus for the disposal of material containing infective microorganisms such as bacteria, fungi and viruses by introducing the material into a container which can be charged with ozone and exposed to the action thereof until the microorganisms are killed, and then the ozone is discharged from the container and converted to a lower valence level and the container is then evacuated.

U.S. Pat. No. 5,700,426 discloses a method for decontaminating or sterilizing "in situ" a vacuum sealed container and device for implementing such method for sterilizing or decontaminating microorganisms or dangerous products.

U.S. Pat. No. 5,841,038 discloses a remote sampling device for possibly hazardous content of a container. A hollow needle punctures the container and is used to withdraw the contents or to introduce another substance. An inert gas can be introduced into the area where the needle punctures the container.

U.S. Pat. No. 5,859,362 discloses a trace vapor detection method and device of sampling a volume of air suspected of containing drug vapors, removing particulate matter and binding vapors of the drug for further analysis. The device has a sampling, filtration and vacuum port components.

U.S. Pat. No. 6,159,422 discloses methods and apparatus for the treatment of hazardous biological waste materials. A biological waste material is placed into a chamber and a vacuum applied. Water vapor is introduced into the chamber and electromagnetic radiation energy is applied to produce a plasma.

U.S. Pat. No. 6,183,950 discloses a method and apparatus for detecting viruses using primary and secondary biomarkers. There is a sampling section for sampling the atmosphere and includes an intake device for taking a sample. It includes a heater for distilling any cholesterol and/or fatty acids from the sample. There is an analysis section for determining whether cholesterol and/or fatty acids that are indicative of the likely presence of a virus in the sample are present.

U.S. Pat. No. 6,295,860 for explosive detection system and sample collecting device in which luggage enters the device and leaves the device after inspection in which a vapor leaking from the luggage is sampled by a sampling probe, negative corona discharge is used to ionize the vapor, and a mass spectrometer is used to detect the ionized vapor to determine whether or not an explosive is present.

Patent Abstracts of Japan Pub. No. 02159554 A published Dec. 12, 1988, Application No. 63313358 discloses a monitoring method of a pathogen or allergen in which a biosensor is provided near a suction port for air conditioning provided for each room of wall surface which tends to gather mold.

WO 91/09307 published Jun. 27, 1991, for Explosive Detection Screening System detects vapor or particulate emissions from explosives and other controlled substances and reports their presence and may also report the concentration. There is a sampling chamber for collection of vapors or other controlled substances and a concentration and analyzing system, and a control and data processing system for the control of the overall system. There are a number of U.S. patents in this series, including the following: U.S. Pat. Nos. 4,987,767; 5,109,691; 5,345,809; 5,465,607; and 5,585,575.

SUMMARY OF THE INVENTION

The U.S. Postal Service has no way of determining if anthrax, or other hazardous materials, are contaminating items of mail. It is desirable to do this before mail enters sorting and distribution centers. A convenient place to do this is in semi-truck trailers (containers) that are loaded with mail from local centers and are trucked to main distribution centers. These containers remain for as much as 24 hours before the mail is removed into the distribution center. This is the time for analysis.

The present invention provides a system and method for detecting hazardous materials inside containers and cargo carriers including semi-trailers, trucks, rail cars, intermodal shipping/cargo containers, and the like.

In one type of system air flow is established within the container to sweep hazardous particles that are entrained in the interior air and dislodge particles from surfaces therein and sweep the particles into a sensor unit for analysis. A shipping container may be provided with at least one wall surface, preferably the floor surface, as an air distribution plenum with air-flow holes or openings therein to allow the establishment of an air flow path within the container. The air flow follows a path upwardly from the floor-located distribution plenum upwardly through the cargo to entrain or otherwise carry or convey particulates, vapors, molecules, or atoms of material upwardly in the container to an exit port or opening. During the time that the air flow pattern is established, a hazardous-materials detection sensor or sensor system is located at or otherwise introduced into the air flow pattern, preferably at or downstream of the air exit port, for a sufficient period of time to sample the flow for a plurality of undesired or hazardous materials.

In another form of the invention, semi-trailers commonly used to ship mail, packages, and other materials are provided with a load-carrying distribution plate that is spaced above the bottom of the trailer body. The distribution plate or surface defines an air distribution plenum therebeneath and includes a plurality of holes distributed across its surface. The air flow pattern can be established by an air-moving fan located within the container or by an auxiliary piece of equipment that connects to the container through an air inlet port and air outlet port to establish a desired air recirculation flow for some period of time. Once the flow has been established, a sensor or sensors are located within the exhaust flow for some period of time sufficient to effect the detection of any undesired or hazardous materials.

The present invention advantageously provides a system and method for quickly and efficiently detecting hazardous materials inside containers typically used to ship materials, including mail, cargo, consumer goods, merchandise, and the like, while the shipped materials are contained and prior to the unloading of the container and possible dissemination/distribution of any hazardous materials.

Other features and advantages will be apparent from the following detailed description of preferred embodiments taken in conjunction with the accompanying drawings.

DESCRIPTION OF THE PREFERRED EMBODIMENTS OF THE INVENTION

Figure 1:
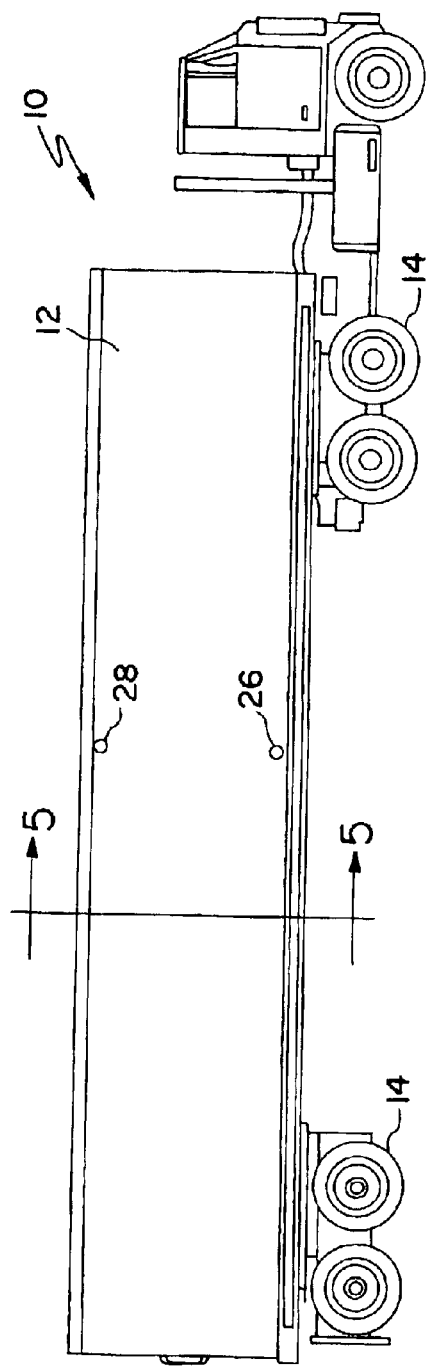
FIG. 1 is a side view of a representative tractor-trailer system including a cargo-carrying trailer incorporating the system of the present invention.
Figure 3:
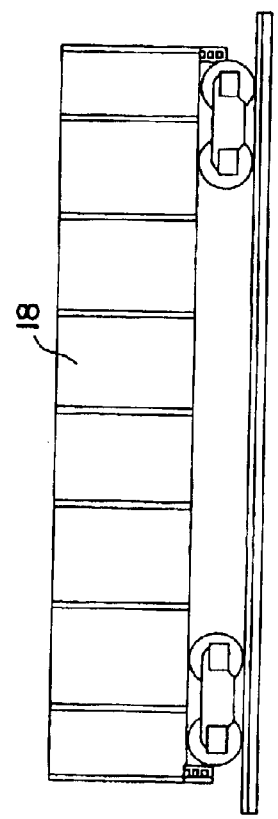
FIG. 3 is a side view of a representative rail car.
Figure 2:
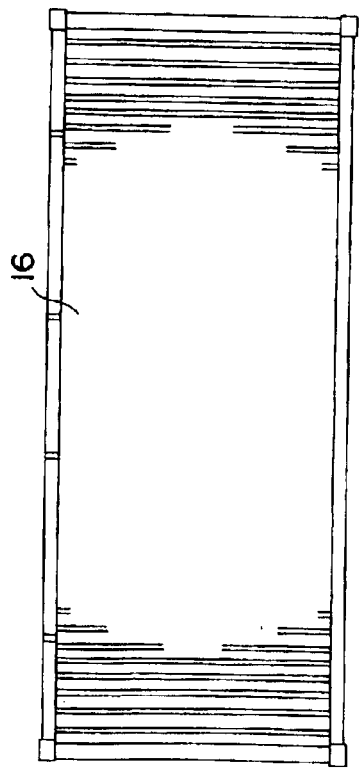
FIG. 2 is a side view of a representative shipping container or cargo box typically used in inter-modal ship/train/truck systems.

A system and method for detecting hazardous materials inside containers in accordance with the present invention is embodied, in part, in shipping containers and cargo boxes typically used to ship letter-mail and packages, manufactured goods, raw materials, and the like and as represented in generic fashion by the semi-trailer of FIG. 1, the shipping container or cargo box of FIG. 2, and the rail car of FIG. 3.

As shown in FIG. 1, a representative semi-trailer 10 includes a conventional trailer body 12 carried on road-wheel assemblies 14. As is known, the trailer body 12 is loaded and unloaded through rearwardly facing doors. As shown in FIG. 2, the representative shipping container 16 is likewise loaded and unloaded through hinged doors at one end and includes various attachment points (not shown) that allow the shipping container 16 to be carried in a stacked relationship on a cargo ship, moved by crane to and shipped by a rail car, and, lastly, mounted on a flat-bed semi-trailer for shipment by roadway. The rail car 18 of FIG. 3, in contrast to the containments of FIGS. 1 and 2, is typically loaded and unloaded via sliding doors on the opposite sides of the car.

Figure 4:
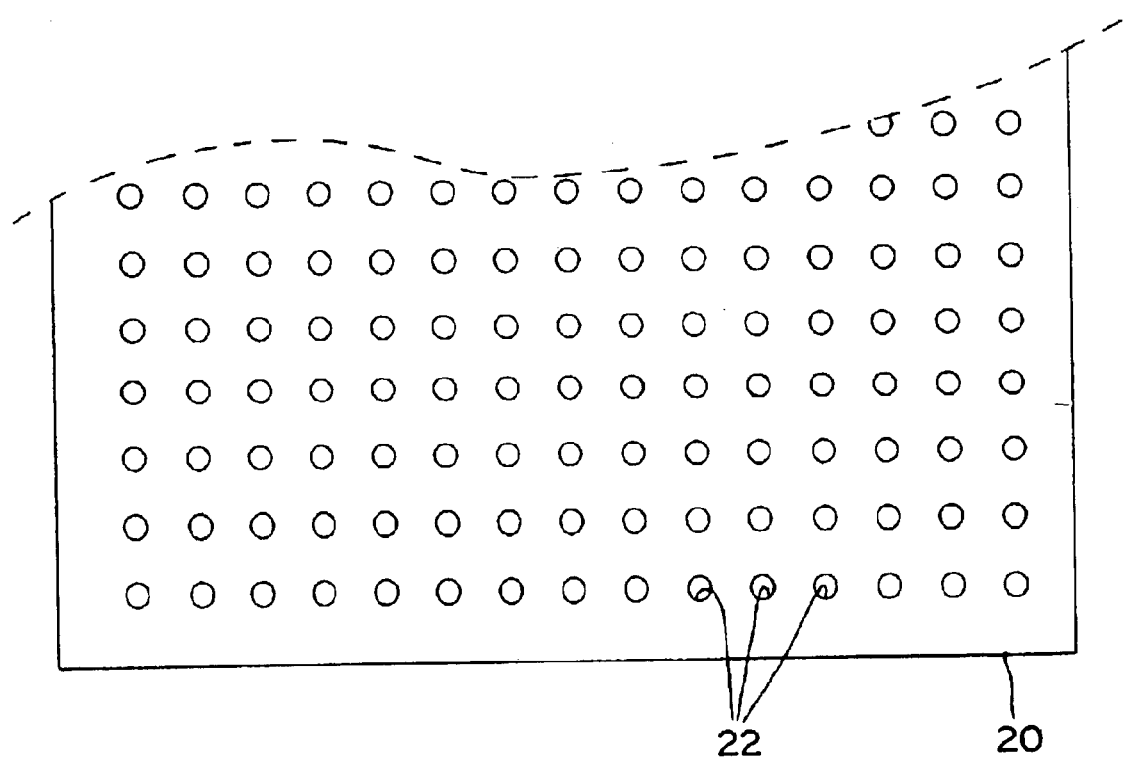
FIG. 4 is a plan view of an air diffuser plate that constitutes a wall surface, such as the load-bearing floor, of the example containers of FIGS. 1–3.

Each of the shipping containments described above is provided with a wall surface, preferably a floor surface that defines part of an air distribution system. More specifically and as shown in FIG. 4, a distribution plate 20 provided with a series of openings or holes 22 that function to distribute a flow of air. For example, the openings can take the form of regularly or irregularly spaced circular holes 22 (as shown in FIG. 4), slots or, for example, cruciform slots of the same or differing size. The distribution plate 20 typically has a surface area co-extensive with that of the load-bearing floor of the container.

Figure 5:
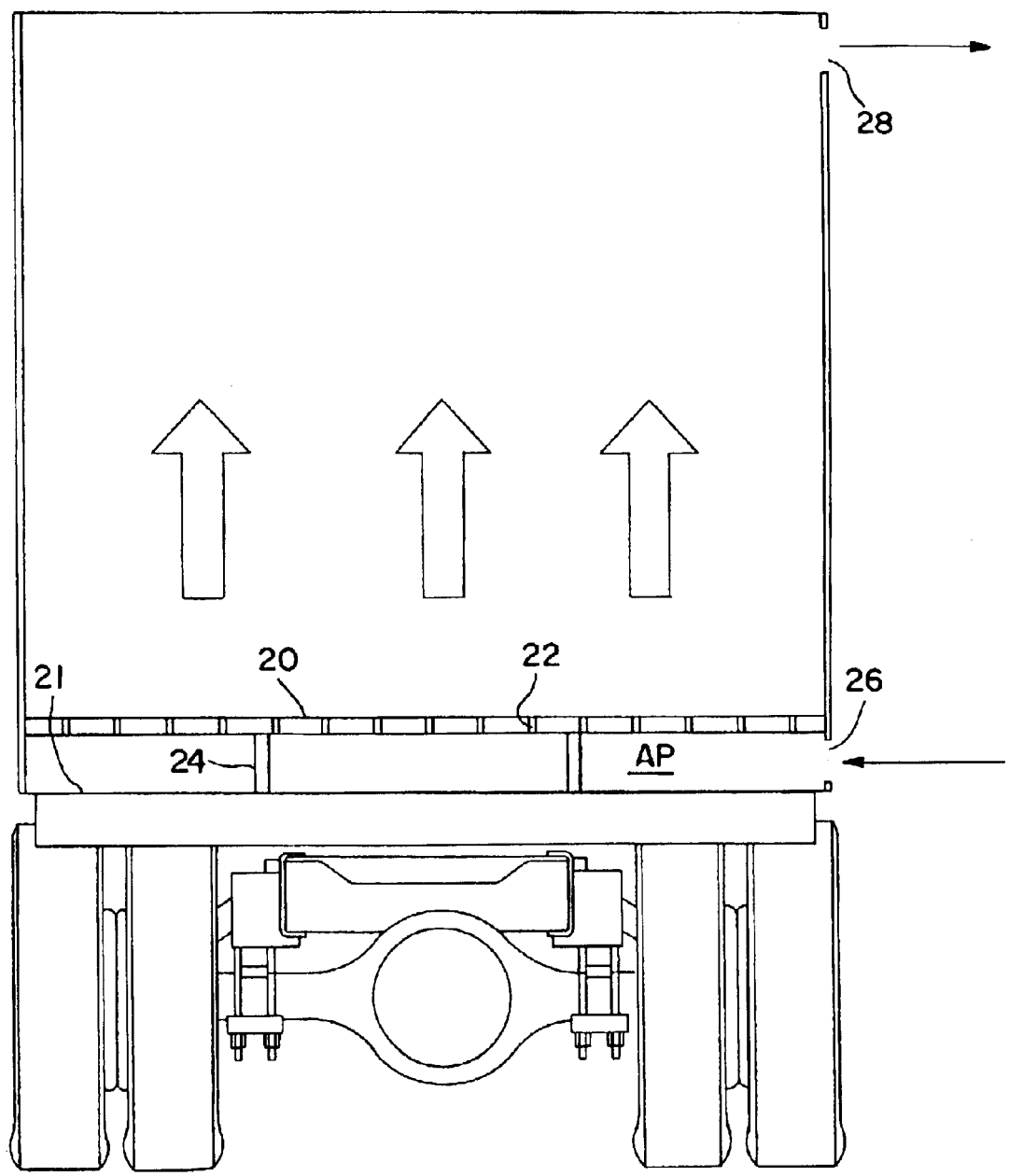
FIG. 5 is a schematic cross sectional view of an exemplary truck trailer container taken generally along the plane defined by reference line 5—5 and showing the air diffuser plate and an air flow upwardly therefrom.

FIG. 5 is a cross sectional view of the semi-trailer of FIG. 1 taken along reference line 5—5 of FIG. 1. The description of FIG. 5 herein also applies to the shipping container or cargo box 16 of FIG. 2 and the rail car 18 of FIG. 3 as well as to any equivalent shipping or cargo containment. As shown in FIG. 5, the distribution plate 20 is spaced above the floor 21 of the semi-trailer and held in place by appropriately spaced beams 24 or joists to define an air distribution plenum AP; for a conventional semi-trailer, a spacing of about 15 or so centimeters (i.e., about 6 inches) above the floor 21 of the semi-trailer 10 is believed sufficient. The semi-trailer 10 is also provided with an air-input port 26 which allows admission of an air flow, as described below, into the air plenum AP as well as an air output port 28 located at or adjacent the upper portion of the semi-trailer 10. The support beams 24 of the air plenum AP, as well as other ducting or baffles (not specifically shown) can function to divide and distribute the input air throughout the air plenum AP so that the input air will be sufficiently and uniformly distributed in the air plenum AP to create a reasonably uniform generally upwardly moving air flow within the semi-trailer 10.

As shown in FIGS. 1 and 5, the air output port 28 is located at or near the top of the semi-trailer 10 and is designed to function as a collection point for some or all of the upwardly directed air flow. The air output port 28 is preferably circular and located intermediate the ends of the semi-trailer. If desired, the air output port 28 can be located in the ceiling of the semi-trailer 10 or at one or the other of the ends thereof. Additionally, it is contemplated that more than one air output port can be used as part of the disclosed system.

Figure 6:
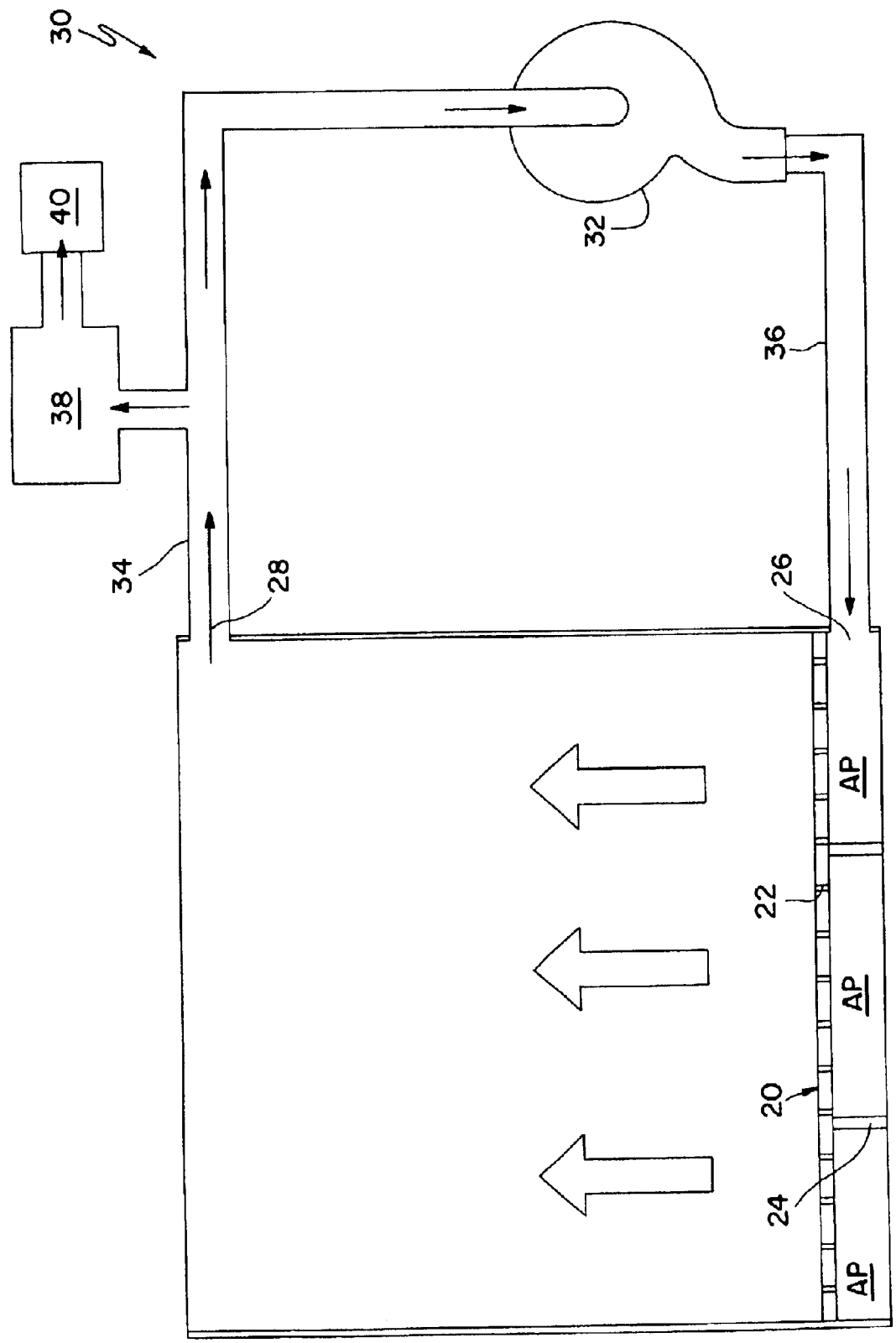
FIG. 6 is an end view of an exemplary container of FIG. 5 and an associated air flow moving system and hazardous-materials sensing system.

As shown in FIG. 6, the semi-trailer is designed to inter-engage with an air recirculation and sensor system 30. As shown, the air recirculation and sensor system 30 includes an air mover 32 having an inlet duct 34 that is selectively connectable to the air outlet port 28 and an outlet duct 36 that is selectively connectable to the air inlet port 26 of the semi-trailer 10. The air mover 32 can take the form, for example, of a single or multi-stage radial flow or axial flow fan having sufficient air moving capability to recirculate the available volume of air within the semi-trailer 10. A sensors suite 38 (typically including a plurality of diverse sensors) is connected to the air inlet duct 34 and is designed to accept at least a portion of the recirculating flow for analysis and thereafter pass the analyzed flow through a filter, adsorber, or scrubber 40.

The sensors could include the Joint Biological Point Detection System (JBPDS) manufactured by Intellitec of Jacksonville, Fla., designed to detect and identify a plurality of biological pathogens. The sensors may include other similar types of fully-integrated, detecting and identifying biological agent sensors, utilizing automated immunoassay methods, that include the 4WARN manufactured by General Dynamics Canada of Calgary, AB, Canada; Portal Shield or JBREWS manufactured by Sentel of Alexandria, Va.; or others. Some sensors could also take the form of a PCR-Nucleic Analysis system such as those manufactured by Cepheid of Sunnyvale, Calif., or Idaho Technologies of Salt Lake City Utah. Some sensors could also take the form of detectors that serve only to detect the presence of biological material in particles in the analyzed air stream, like the BIONI, manufactured by Pacific Scientific Instruments of Grant's Pass, Oreg.; the Biological Aerosol Warning System Tier III developed by MIT Lincoln Laboratories in MA; the UV-APS, manufactured by TSI Inc. of St. Paul, Minn.; the UV-FLAPS and BARTS manufactured by General Dynamics Canada of Calgary, AB, Canada; or others. The sensors could also include a particle detector-based system like the Biological Aerosol Warning System Tier I, manufactured by Lockheed Martin of Manassas, Va.

In addition, a simple collector, such as a filter or a BioCapture system manufactured by Mesosystems, Inc of Kennewick, Wash.; or other type of particle capture device could also be part of the sensor suite. Such a unit would be intended to capture particles for later laboratory analyses, including culturing, immunoassay, and PCR-nucleic acid methods. Such a unit would also be useful for forensic purposes and for the collection of evidence. The sensor suite could also include one or more chemical warfare agent sensors such as ion mobility spectrometers including the ChemPro 100 or the M-90 manufactured by Environics Oy of Mikkeli, Finland, or similar sensors manufactured by Graseby Ionicics and ETG; surface acoustic wave sensor-based devices including the JCAD sensor, manufactured by BAE Systems of San Antonio, Tex.; the HAZMATCAD, manufactured by Microsensor Systems Inc. of Bowling Green, Ky.; the Micro Chem Lab on a Chip manufactured by Sandia National Laboratories in Albuquerque, N.Mex.; the SnifferSTAR sensor manufactured by Lockheed Martin of Manassas, Va. and Sandia National Laboratories; or others. They could also take the form of explosives sensors, such as those manufactured by Ion Track Instruments of MA or Smith's Sensors of NJ (formerly Barringer), or contraband drugs sensors manufactured by the latter two manufacturers. The sensors could also include sensors for radiological particles in air, including Geiger counters and other radiological detectors. A plurality of detectors will generally be used.

It is envisioned that one use of the disclosed embodiments is in the detection of biological pathogens, such as anthrax spores, in the mail system. More particularly, mail trucks, including both mail carrying semi-trucks and other mail trucks having a separate and defined cargo containment, will move mail in the usual manner. Prior to unloading of the vehicle, the air inlet duct 34 and the air outlet duct 36 of the air recirculation and sensor system 30 are connected to the semi-trailer 10 through the appropriate ports as discussed above. The air mover 32 is operated to establish a recirculation flow from the distribution plate 20 upwardly through the interior air space of the containment. In general, the air flow circulation is maintained until sufficient time has elapsed, usually a period of minutes, to cause any air entrainable particles, including bacteria, bacterial spores, viruses, rickettsia, toxins, low volatility chemical particles including chemical warfare agent particles like VX, explosives particles, particles of illicit drugs, radioactive particles, and others, as well as vapors including chemical warfare agents, explosives and explosives related compounds, illicit drugs, hazardous industrial chemicals, and others, to enter and diffuse into some of the available interior air and the air flow. After a suitable period of time, the sensor system 38 is then operated to sample the air flow to determine the presence or absence of hazardous or otherwise undesirable matter in the contained cargo.

In the disclosed embodiment, the distribution plate 20 has been shown mounted above the usual load-carrying floor 21 of the semi-trailer 10. As can be appreciated, other configurations are contemplated. For example, the distribution plate 20 and the associated air plenum AP can be mounted as part of the ceiling of the cargo containment to establish a top down air flow, in one side wall or the other to define a side to side air flow, and/or in an end wall of the containment to define an air flow that moves from one end to the other end of the cargo containment.

The present invention advantageously provides a system and method for detecting hazardous materials inside containers used to ship or convey mail, manufactured goods, raw materials, and the like with a minimum of costs and time.

However, the present invention is particularly usable to detect and identify harmful particulate or vapor materials, including anthrax, in a container, such as a semi-truck's trailer, full of U.S. mail. The diffuser plate is placed on the floor of the mail trailer. The diffuser plate may be of steel running the full length and width of the container, with holes in it, which may, for example, be ½ inch holes. The plate can be supported about 6" above the trailer's floor, although particular arrangements may require a greater or lesser space. This plate becomes a permanent part of the container. The mail is then loaded in on top of this plate and the container transported to a sorting and distribution center.

A vehicle is driven up to the container to analyze it for anthrax or other contaminants including other biological warfare agents, chemical warfare agents, radiological materials, explosives vapors or particles, and the like. This vehicle has an air blower, or other air moving means, attached to it. The outlet of this blower connects to a fitting in the side or bottom of the container that leads the pressurized air under the diffuser plate. The inlet to this blower attaches to the headspace above the mail. The purpose of the blower is to pass air through the mail in a recirculating fashion, sweeping any biological particles, including anthrax, and any chemical warfare agent gases, radiological particle, etc., into the blower's inlet.

If the air stream is fast enough the mail may be agitated in the way that gas flows and diffuser plates are used to agitate particles in a fluidized catalyst bed. The inlet or outlet to the pump may also have a biological warfare agent sensor (which is especially useful to solve the current anthrax problem in connection with the U.S. Postal Service) and, if desired possibly some other sensors including chemical warfare agent, radiological, explosives, and the like, attached to it. This JBPDS (or other) sensor detects biological particles in a few seconds and, if they are present, it collects a 5 minute air sample (this is just an example of the time, and the particular arrangement may require a greater or lesser amount of time), and then use its specific identifier to determine whether or not anthrax or some other specific agent were present. If other detectors are included, they simultaneously analyze for the other materials listed above. This should solve the postal service problem of letting anthrax contaminated mail into mail sorting and distribution centers.

Also, some gentle agitation may be provided in the mobile type of containers (trucks and rail cars, e.g.) as the vehicle moves toward its destination, caused by the natural movement up and down and side to side that occurs with such vehicles.

It should be noted that in order to prevent contaminated air from entering the ambient atmosphere, the container may be sealed and the air connections to the container and the air blower and other connections also sealed to prevent the air from escaping into the ambient atmosphere before testing for hazardous materials has been completed.

Also, if the container cannot be completely sealed, or for other reasons, instead of using an air blower, a vacuum generator may be connected so that the container will have a slight under pressure when compared to the ambient atmosphere (a level of under pressure consistent with the structural stability of the container) and therefore will not force air from inside the container to the ambient atmosphere, but, rather will bring some ambient air into the container in the event it is not completely air tight. Some, but not all, of the sensors discussed above would function properly when placed on the line that connects the container with the vacuum generator.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A system for detecting hazardous materials in mail and the like, comprising:
   a. an enclosed chamber in a container which is sealed with respect to the ambient atmosphere for containing mail;
   b. an air plenum associated with one surface of the container and having an air distributor for providing an air flow within the chamber;
   c. air input and output ports for accepting a flow of air for distribution within the container, and through-out the mail contained therein, and for directing the flow of air therefrom for entraining particulates; and
   d. a hazardous materials detection system for detecting the presence of one or more hazardous materials in the air flow.

2. A system as defined in claim 1, wherein said chamber, plenum, ports and detection system are sealed so that air may not escape therefrom into the ambient atmosphere before detecting for the presence of hazardous materials.

3. A system as defined in claim 2, wherein said hazardous materials detection system includes sensors for sensing one or more of biological pathogerts including bacteria, bacterial spores, viruses, rickettsia, toxins, low-volatility chemical particles including chemical warfare agents, VX particles, explosives particles, particles of, or particles associated with, illicit drugs, and other biological particles and materials, and radioactive particles, chemical vapors including chemical warfare agents, explosives and explosives-related compounds, illicit drugs, hazardous industrial materials, other chemical vapors and materials, and other hazardous materials.

4. A system as defined in claim 2 further comprising means for agitating the mail to loosen particles and vapors therefrom to assure that they are entrained in the air flow.

5. A system as defined in claim 4 wherein said agitating means includes an air flow generator to provide air at a sufficient velocity to agitate the mail.

6. A system as defined in claim 4 wherein said container is a semi-trailer, a rail car or a mail container.

7. A system as defined in claim 2 further comprising an air flow generator.

8. A system as defined in claim 7 wherein said air flow generator creates an under-pressure at the air inlet.

9. A system for detecting hazardous materials comprising:

a cargo containment for containing a cargo;

an air plenum associated with one surface of the interior of the cargo containment and having an air distribution means for distributing an air flow within the containment;

air input and output ports for accepting a flow of air for distribution within the containments, and through the mail contained therein, and for directing the flow of air therefrom; and a materials detection system for detecting the presence of one or more materials in the air flow.

10. The system of claim 1, wherein said materials detection system includes sensors for sensing one or more of biological pathogens including backeria, bacterial spores, viruses, rickettsia, toxins, low-volatility chemical particles including chemical warfare agents, VX particles, explosives particles, particles of, or particles associated with, illicit drugs, and other biological particles and materials, and radioactive particles, chemical vapors including chemical warfare agents, explosives and explosives-related compounds, illicit drugs, hazardous industrial materials, other chemical vapors and materials, and other hazardous materials.

11. A method for detecting hazardous materials in mail, comprising the steps of:

a. providing an airtight container for holding mail and having at least one air inlet and at least one air outlet;

b. moving air through the container and through the mail contained therein between said air inlet and said air outlet;

c. providing at least one hazardous material sensor; and d. directing air leaving the container to said sensor.

12. A method as defined in claim 11, further comprising the steps of:

e. analyzing the air in or leaving the container for at least trace amounts of hazardous materials; and f. providing an alert signal when the air being analyzed contains at least trace amounts of hazardous material.

13. A method as defined in claim 12, further comprising the step of:

g. agitating the mail in the container sufficiently to dislodge at least a trace amount of any hazardous material contained therein or thereon.

14. A method as defined in claim 12 wherein the step of moving air creates an under-pressure at the air outlet.

15. A method as defined in claim 12 wherein the step of moving air creates an over-pressure at the air inlet.

16. A method as defined in claim 12 wherein the method is carried out in the absence of a heating treatment.

17. The system of claim 1 wherein said air distributor includes a sub-floor having holes throughout for distributing the air flow through the mail contained therein.

* * * * *